United States Patent
Köhler et al.

(10) Patent No.: US 7,351,678 B2
(45) Date of Patent: Apr. 1, 2008

(54) CATALYST SYSTEMS FOR ZIEGLER-NATTA PROPENE POLYMERISATION

(75) Inventors: Kartin Köhler, Dossenheim (DE); Herbert Schumann, Berlin (DE); Birgit Corinna Wassermann, Berlin (DE); Wilfried Wassermann, Berlin (DE); Katharina Lange, Berlin (DE); Sebastian Dechert, Berlin (DE); Markus Hummert, Berlin (DE); Stefan Schutte, Berlin (DE); Walter Kaminsky, Pinneberg (DE); Andrea Eisenhardt, Hamburg (DE); Björn Heuer, Hamburg (DE); Andre Laban, Klein Nordende (DE)

(73) Assignee: Merck Patent GmbH, Darmstadt (DE)

(*) Notice: Subject to any disclaimer, the term of this patent is extended or adjusted under 35 U.S.C. 154(b) by 154 days.

(21) Appl. No.: 10/491,917

(22) PCT Filed: Sep. 11, 2002

(86) PCT No.: PCT/EP02/10171

§ 371 (c)(1), (2), (4) Date: Apr. 8, 2004

(87) PCT Pub. No.: WO03/031454

PCT Pub. Date: Apr. 17, 2003

(65) Prior Publication Data

US 2004/0242408 A1    Dec. 2, 2004

(30) Foreign Application Priority Data

Oct. 9, 2001    (DE) ................. 101 49 785

(51) Int. Cl.
| | |
|---|---|
| B01J 31/14 | (2006.01) |
| B01J 31/00 | (2006.01) |
| B01J 31/18 | (2006.01) |
| C07F 5/00 | (2006.01) |
| C07F 5/06 | (2006.01) |
| C08F 4/52 | (2006.01) |
| C08F 4/658 | (2006.01) |
| C08F 10/00 | (2006.01) |
| C08F 10/06 | (2006.01) |

(52) U.S. Cl. ............ 502/103; 502/102; 502/115; 502/117; 502/118; 502/125; 502/127; 526/124.3; 526/125.3; 526/128; 526/142; 526/151; 526/348; 556/9; 556/27; 556/51; 556/175; 556/176

(58) Field of Classification Search ........... 502/103, 502/117, 118, 125, 127; 556/176, 9, 27, 556/51, 175; 526/163, 124.3, 125.3, 128, 526/142, 151, 348

See application file for complete search history.

(56) References Cited

FOREIGN PATENT DOCUMENTS

| DE | 43 06 569 | 9/1994 |
|---|---|---|
| EP | 0 919 557 | 6/1999 |
| EP | 1 132 409 | 9/2001 |

OTHER PUBLICATIONS

Chemical Abstract No. 1990:631443 (112:231443), abstract of an article by Schumann et al. entitled "Intramolecularly Stabilized Organoaluminum, -gallium and -indium derivatives", (Chemische Berichte 123 (1), pp. 2093-2099 (1990), no month.*

* cited by examiner

Primary Examiner—Anthony J. Green
(74) Attorney, Agent, or Firm—Millen, White, Zelano, Branigan, P.C.

(57) ABSTRACT

The invention relates to the use of nitrogenous aluminium organyl complexes of general formula (I) as co-catalysts in heterogeneous polymerisation reactions of propene. In said formula: R, R', $R^1$ and $R^{1'}$ independently of one another represent branched or unbranched $C_1$-$C_7$ alkyl, cycloalkyl, alkenyl, cycloalkenyl, aryl or alkynyl; $R^2$ represents unsubstituted, monoalkylated or polyalkylated and/or monofluorinated or polyfluorinated aromatic hydrocarbons from group (II); $R^3$ and $R^4$ independently of one another represent $CH_2$, $CF_2$ oder $C(R^1)_2$; m stands for 0, 1 or 2; n stands for 0, 1 or 2; o stands for 0 or 1, all independently of one another. Said systems exhibit improved characteristics in terms of activity and stereoselectivity in comparison to conventional co-catalysts such as $AlEt_3$ and can act simultaneously as co-catalysts and stereoselectivity promoters 16 Claims, 3 Drawing Sheets

CATALYST SYSTEMS FOR ZIEGLER-NATTA PROPENE POLYMERISATION

Figure 1:
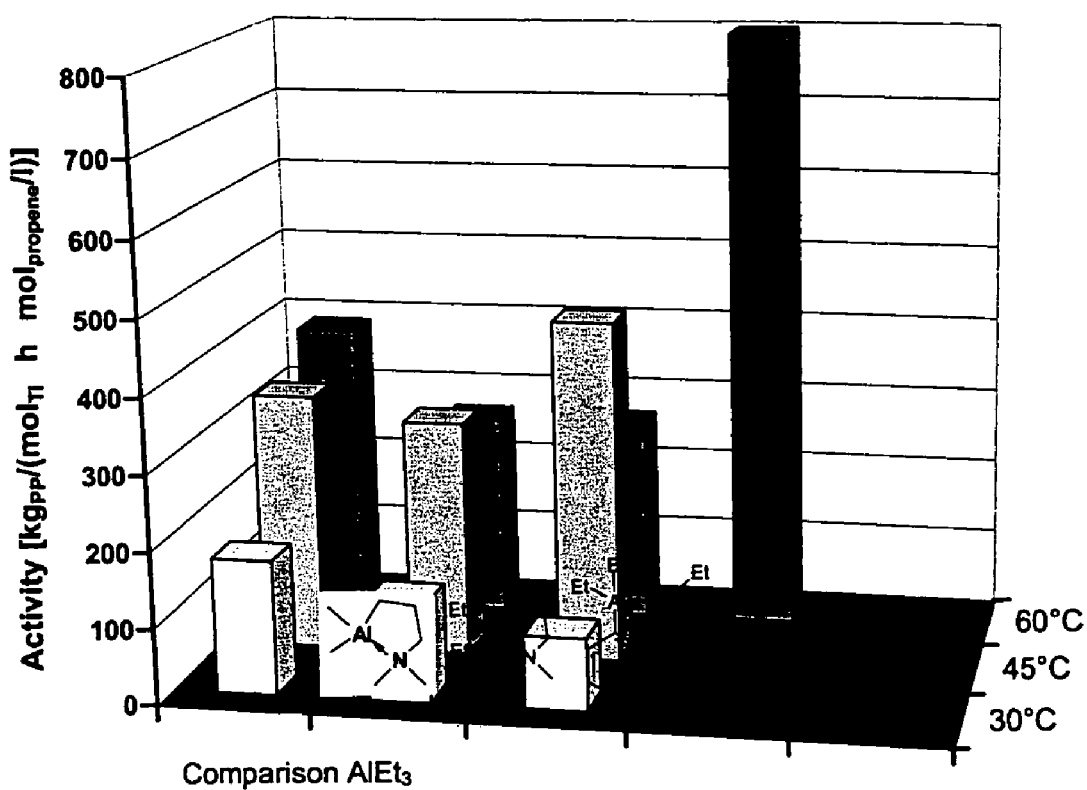

The present invention relates to the use of nitrogen-containing organoaluminium complexes of the general formula (I)

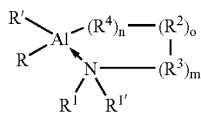
(I)

in which

R, R', $R^1$ and $R^{1'}$, independently of one another, are branched or unbranched $C_1$-$C_7$-alkyl, -cycloalkyl, -alkenyl, -cycloalkenyl, -aryl or -alkynyl;

$R^2$ is an unsubstituted, mono- or polyalkylated and/or mono- or polyfluorinated aromatic hydrocarbon from the group consisting of

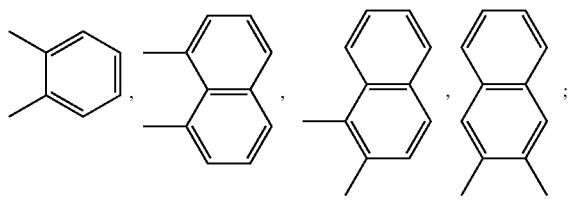

$R^3$ and $R^4$, independently of one another, are $CH_2$, $CF_2$ or $C(R^1)_2$;

independently of one another m is 0, 1 or 2, n is 0, 1 or 2, and o is 0 or 1, as cocatalysts in heterogeneous polymerisation reactions for the polymerisation of propene. These systems have improved properties with respect to activity and stereoselectivity compared with cocatalysts conventionally employed, such as $AlEt_3$, and can at the same time act as cocatalysts, but also as stereoselectivity promoters.

Ziegler-Natta-catalysed polymerisation is a polymerisation process which has constantly been improved over a number of generations since the initiating work by Ziegler and Natta in the 1950s. Increasing both the activity and the stereoselectivity are the driving criteria for the continuous development of the catalyst system. The catalyst systems for the polymerisation of 1-alkenes have in the meantime been divided into five generations [E. Albizatti, U. Giannini, G. Collina, L. Noristi, L. Resconi, *Polypropylene Handbook*, E. P. Moore (Ed.), Hanser Publishers, Munich, 1996, 11].

| Genera-tion | Composition | Productivity[a] [$kg_{pp}/g_{catalyst}$] | Isotacticity Index | Morphology control |
|---|---|---|---|---|
| 1. | δ-$TiCl_3$0.33$AlCl_3$ + $AlEt_2Cl$ | 0.8-1.2 | 90-94 | not possible |
| 2. | δ-$TiCl_3$ + $AlEt_2Cl$ | 3-5 (10-15) | 94-97 | possible |
| 3. | $TiCl_4$/ester/$MgCl_2$ + $AlR_3$/ester | 5-10 (15-30) | 90-95 | possible |
| 4. | $TiCl_4$/diester/ $MgCl_2$ + $AlEt_3$/silanes | 10-25 (30-60) | 95-99 | possible |
| 5. | $TiCl_4$/diether/ $MgCl_2$ + $AlEt_3$ | 25-35 (70-120) | 95-99 | possible |

[a]Polymerisation: Hexane slurry, 70° C., 7 bar of propene, 4 hours, $H_2$ for molecular weight regulation (values in parentheses originate from polymerisations in bulk, 2 hours, 70° C., $H_2$).

The established system of today is based on the use of multicomponent catalysts. In addition to the support material, these include, as the actual catalyst, a transition-metal compound, for example a titanium compound, which is first activated by addition of an aluminium-containing cocatalyst. In addition, further constituents, such as internal and external donors, are necessarily required. The use of an internal donor here prevents agglomeration of the catalytically active species, while the external donor improves the stereospecificity on use of prochiral olefins. As can be seen from the table, a continuous improvement process has taken place in recent decades, in which, up to the fifth generation, in particular the surface areas of the supported catalysts have been increased and the proportion of a specifically working centres has been reduced [P. Pino, R. Mülhaupt, *Angew. Chem.* 1980, 92 (11), 869; M. Boreo, M. Parrinello, S. Hüffer, H. Weiss, *J. Am. Chem. Soc.* 2000, 122, 501]. These catalyst systems save expensive separation of catalyst residues and complex extraction of atactic components from the polyolefins prepared. The understanding that has now been attained on the correlation between catalyst and polymer morphology enables control of the polymer morphology during the polymerisation process, which eliminates additional processing steps, such as extrusion and granulation. Without the advances, solvent-free gas-phase polymerisation and polymerisation in bulk would not have been possible at all, and they have resulted in significant simplifications in suspension polymerisation [P. Galli, J. C. Haylock, *Makromol. Chem., Macromol. Symp.* 1992, 63, 19-54; P. Corradini, V. Buscio, G. Guerra, in *Comprehensive Polymer Science*, Vol. 4, G. Allen (Ed.), Pergamon Press, 1989, p. 29; C. Jenny, P. Maddox, *Solid State & Mat. Science* 1998, 3, 94; K. Soga, T. Shiono, *Progress in Polymer Science* 1997, 22, 1503].

The most important cocatalysts preferably used are alkylaluminium compounds, such as $AlEt_3$, $Al$-$i$-$Bu_3$, $AlEt_2Cl$, $AlEtCl_2$ and $AlEt_2OR$, all of which are very sensitive to atmospheric oxygen and moisture and are therefore difficult to handle. Besides the titanium chlorides, catalysts of interest are, in particular, compounds of vanadium and chromium, also molybdenum, cobalt, rhodium and nickel in specific applications. Instead of the alkylaluminium compounds, numerous other organometallic compounds, in particular of sodium, lithium and cadmium, have been described as effective in combination with titanium compounds (H. J. Sinn et al., Polymerisation und Insertionsaktivität von Aluminium-trialkylen und Ziegler-Natta Katalysatoren [Polymerisation and Insertion Activity of Trialkylaluminium Compounds and Ziegler-Nafta Catalysts], *Angew. Chem.* 72 (1960) 522).

Besides achievement of the desired product properties, further factors are crucial for assessment of the performance of a coordination catalyst system, for the preparation of polymers, such as the activity of the catalyst system, i.e. the amount of catalyst necessary for economic conversion of a prespecified amount of olefin, the product conversion per time unit and the product yield, the loss of catalyst and the reusability of the catalyst. There is therefore a demand for catalyst systems having the highest possible productivity, but also high specificity in favour of a low degree of branching and high stereoregularity of the polymer.

Also essential, however, is the question of stability and handling ability of the catalyst or its components. Ingress of (atmospheric) oxygen and/or water reduces the activity of conventional catalysts or irreversibly destroys them. The catalysts therefore have to be stringently protected against the ingress of air and moisture during preparation, storage and use, which naturally makes handling more difficult and increases the requisite effort.

Conventional catalyst systems are also sensitive to substances containing electron-rich elements, such as, for example, oxygen or nitrogen, in the molecule. Compounds such as ethers and amines, but also polar monomers which may be of interest as comonomers or additives for the polymer, deactivate the catalyst.

Still more sensitive in this respect and therefore even more difficult to handle are the organometallic compounds to be employed as activators or cocatalysts, such as, in particular, the alkylaluminium compounds predominantly used for this purpose. These very compounds represent a serious problem owing to their extreme sensitivity and self-combustibility in practice.

DE 19753135 has described a number of aluminium compounds which are distinguished by an intramolecular donor side chain, for example an amino-, thio- or oxo-coordinated side chain, which can be prepared by methods known to the person skilled in the art for the preparation of organometallic compounds. These aluminium compounds act as cocatalytically activating components in Ziegler-Natta catalysts for the polymerisation of ethylene. However, the polymerisation of propylene or higher α-olefins does not succeed with the catalyst systems described in this patent application. It was subsequently described in DE 10010796 that the compounds described in DE 19753135 can be used for the polymerisation of propylene if they are supported on MgCl$_2$ with addition of TiCl$_4$ or on use of MgCl$_2$/TiCl$_4$. However, the catalyst systems used therein do not achieve the productivities or activities obtained by means of conventional Ziegler-Natta catalyst systems (MgCl$_2$/TiCl$_4$AlEt$_3$).

The following factors were in need of improvement:

a) In order to be able further to increase the yield of polymers in the polymerisation of propene, catalyst systems having higher activities have to be customised and developed. It should be possible to achieve the increase in activity by optimisation of the cocatalyst, since it converts the catalyst into the species which is actually catalytically active and continually reactivates it. This interaction between catalyst and cocatalyst is crucial for the efficiency of the catalyst system as a whole.

b) The catalyst systems used on an industrial scale comprise highly pyrophoric, reactive, volatile alkylaluminium compounds as cocatalysts, in particular triethylaluminium. These compounds have high sensitivity to impurities in the reaction medium, such as, for example, to residual moisture of the monomers to be polymerised. In addition, safe handling of such highly pyrophoric and volatile compounds requires complex safety containers for their storage and for their transport with absolute exclusion of oxygen and moisture. Furthermore, the industrial-scale plants for catalyst preparation and polymerisation must be geared to this problem. This is, in particular, a problem for industrially less developed countries and regions in which, owing to the climate, high temperatures and high atmospheric humidity levels prevail.

c) In order to achieve high stereoselectivities in the Ziegler-Natta catalysis of prochiral olefins, expensive external donors, such as, for example, PhSi(OEt)$_3$, additionally have to be employed in many processes. It has hitherto not been possible to optimise to full satisfaction the properties of the resultant polymers, which are determined, inter alia, by branching rates, tacticities, molecular weights and molecular-weight distributions, which gives rise to a constant demand for polymers having improved, but also novel properties.

d) Since the cocatalyst in Ziegler-Natta catalysts is usually employed in high excesses to the catalyst and is thus the most expensive component, there is great interest in reducing the cocatalyst/catalyst ratio while retaining the activity and stability of the catalytically active species.

The object of the present invention is therefore to provide catalyst systems for the homopolymerisation of propene which do not have the properties or disadvantages listed under a), b), c) and d). A further object of the present invention was to provide in a simple and inexpensive manner corresponding catalyst systems which are bonded to suitable supports. It should be possible to employ the catalyst systems according to the invention in industrial-scale plants under simple conditions with a lower cocatalyst/catalyst ratio and at the same time they should have higher activities than systems known hitherto. A further object of the present invention is to provide corresponding catalyst systems which are less sensitive to impurities, in particular to moisture.

The object is achieved by the use of nitrogen-containing organoaluminium complexes of the general formula (I)

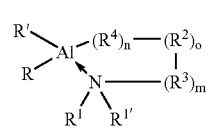

(I)

in which

R, R', R$^1$ and R$^{1'}$, independently of one another, are branched or unbranched C$_1$-C$_7$-alkyl, -cycloalkyl, -alkenyl, -cycloalkenyl, -aryl or -alkynyl;

R$^2$ is an unsubstituted, mono- or polyalkylated and/or mono- or polyfluorinated aromatic hydrocarbon from the group consisting of

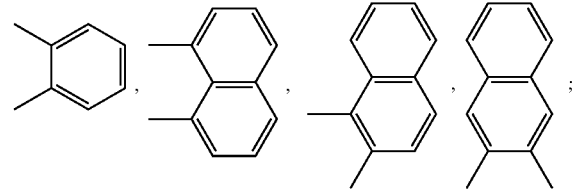

R$^3$ and R$^4$, independently of one another, are CH$_2$, CF$_2$ or C(R$^1$)$_2$;

independently of one another m is 0, 1 or 2, n is 0, 1 or 2, and o is 0 or 1, as components in coordination catalysts for the polymerisation of propene.

Some of these specific compounds are novel, while others are described in the literature. The use of these compounds for the polymerisation of propene is not described in the examples published by Patent Application DE 19753135.

The object on which the invention is based is achieved, in particular, by the use of compounds of the general formula (I) in which R, R', R' and R", independently of one another, are branched or unbranched $C_1$-$C_7$-alkyl, $R^2$ is an unsubstituted hydrocarbon from the group consisting of

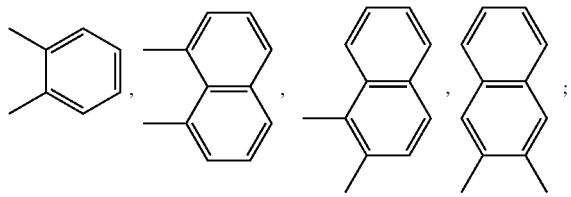

$R^3$ and $R^4$, independently of one another, are $CH_2$, $CF_2$ or $C(R^1)_2$; and independently of one another
m is 0, 1 or 2,
n is 0, 1 or 2, and
o is 0 or 1.

From this group of compounds, those in which $R^2$ is selected from the group consisting of

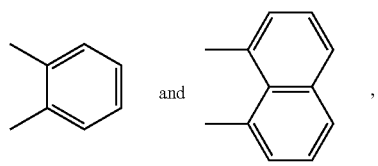

give particularly good results.

From this group of complexes, compounds of the general formula (I) in which
$R^1$ and $R^{1'}$ are $CH_3$ and
R and R', independently of one another, are i-$C_3H_7$, i-$C_4H_9$ or a branched or unbranched alkyl from the group consisting of $C_5H_{11}$, $C_6H_{13}$ and $C_7H_{15}$ have in turn proven particularly suitable for use as catalyst component in the polymerisation of propene.

Equally suitable are also complexes
in which
$R^1$ and $R^{1'}$ are $C_2H_5$ and
R and R', independently of one another, are branched or unbranched $C_1$-$C_7$-alkyl.

Particularly good results are achieved through the use of nitrogen-containing organoaluminium complexes of the general formula (I) in which
R and R', independently of one another, are $CH_3$, $C_2H_5$ or i-$C_4H_9$,
$R^1$ and $R^{1'}$, independently of one another, are $CH_3$ or $C_2H_5$,
$R^2$ is an unsubstituted hydrocarbon selected from the group consisting of

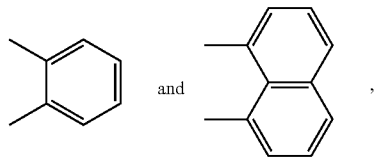

$R^3$ and $R^4$ are $CH_2$, and m and n=0 or 1, and o=1.

Improved catalyst activities are preferably achieved using complexes of the general formula (I)

in which
R, R', $R^1$ and $R^{1'}$, independently of one another, are branched or unbranched $C_1$-$C_7$-alkyl,
$R^2$ is

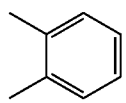

$R^3$ is $CH_2$,
m and o are 1, and
n is 0.

Nitrogen-containing organoaluminium complexes of the general formula (I)
in which
$R^1$ and $R^{1'}$ are $CH_3$ and
R and R', independently of one another, are branched or unbranched $C_3$-$C_7$-alkyl, or
$R^1$ and $R^{1'}$ are $C_2H_5$ and
R and R', independently of one another, are branched or unbranched $C_1$-$C_7$-alkyl,
$R^2$ is

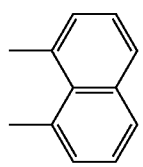

o is 1, and
m and n are 0, give comparable results.

Corresponding nitrogen-containing organoaluminium complexes can be employed per se as cocatalysts in olefin polymerisation reactions.

It has been found that, in particular, compounds of the general formula
(I) selected from the group consisting of
[3-(dimethylamino)propyl]dimethylaluminium,
[3-(dimethylamino)propyl]diethylaluminium,
[3-(dimethylamino)propyl]dipropylaluminium,
[3-(dimethylamino)propyl]dibutylaluminium,
[3-(diethylamino)propyl]dimethylaluminium,
[3-(diethylamino)propyl]diethylaluminium,
[3-(diethylamino)propyl]dipropylaluminium,
[3-(diethylamino)propyl]dibutylaluminium,
[4-(dimethylamino)butyl]dimethylaluminium
[4-(dimethylamino)butyl]diethylaluminium

[4-(dimethylamino)butyl]dipropylaluminium
[4-(dimethylamino)butyl]dibutylaluminium
[4-(diethylamino)butyl]dimethylaluminium
[4-(diethylamino)butyl]diethylaluminium
[2-(dimethylamino)phen-1-yl]dimethylaluminium,
[2-(dimethylamino)phen-1-yl]diethylaluminium,
[2-(dimethylamino)phen-1-yl]dipropylaluminium,
[2-(dimethylamino)phen-1-yl]dibutylaluminium,
[2-(diethylamino)phen-1-yl]dimethylaluminium,
[2-(diethylamino)phen-1-yl]diethylaluminium,
[2-(dimethylamino)benzyl]dimethylaluminium,
[2-(dimethylamino)benzyl]diethylaluminium,
[2-(dimethylamino)benzyl]dipropylaluminium,
[2-(dimethylamino)benzyl]dibutylaluminium,
[2-(diethylamino)benzyl]dimethylaluminium,
[2-(diethylamino)benzyl]diethylaluminium,
[2-(dimethylaminomethyl)phen-1-yl]dimethylaluminium,
[2-(dimethylaminomethyl)phen-1-yl]diethylaluminium,
[2-(dimethylaminomethyl)phen-1-yl]dipropylaluminium,
[2-(dimethylaminomethyl)phen-1-yl]dibutylaluminium,
[2-(diethylaminomethyl)phen-1-yl]dimethylaluminium,
[2-(diethylaminomethyl)phen-1-yl]diethylaluminium,
[2-(diethylaminomethyl)phen-1-yl]dipropylaluminium,
[2-(diethylaminomethyl)phen-1-yl]dibutylaluminium,
[8-(dimethylamino)naphth-1-yl]dimethylaluminium,
[8-(dimethylamino)naphth-1-yl]diethylaluminium,
[8-(dimethylamino)naphth-1-yl]dipropylaluminium and
[8-(dimethylamino)naphth-1-yl]dibutylaluminium, can be employed as components in coordination catalysts in propene polymerisation reactions.

Experiments have shown that, in particular, the novel compounds selected from the group consisting of
[2-(dimethylaminomethyl)phen-1-yl]dimethylaluminium,
[2-(dimethylaminomethyl)phen-1-yl]diethylaluminium,
[2-(diethylaminomethyl)phen-1-yl]diethylaluminium,
[2-(dimethylamino)benzyl]diethylaluminium and
[8-(dimethylamino)naphth-1-yl]dimethylaluminium are suitable for this purpose and give very good polymerisation results.

Compounds of the general formula (I) can therefore advantageously be employed in accordance with the invention as components in coordination catalysts in heterogeneous propene polymerisation reactions.

The product properties can particularly advantageously be influenced by the addition of these compounds since they can be employed specifically as stereoselectivity promoters in the polymerisation of propene.

In accordance with the invention, the novel coordination catalysts for polymerisation reactions comprise nitrogen-containing organo-aluminium complexes of the general formula (I), in combination with transition-metal compounds from sub-groups IV to VIII of the Periodic Table of the Elements. These are preferably compounds selected from the group consisting of the halides of titanium and vanadium. These compounds represent per se the actual catalysts in the polymerisation reaction.

In accordance with the invention, the nitrogen-containing organoaluminium complexes of the general formula (I), can be used as cocatalysts in olefin polymerisation reactions.

This system consisting of coordination catalyst and catalyst is usually bonded to a support material. The catalyst system according to the invention is preferably bonded to an inorganic support selected from the group consisting of $MgCl_2$ and $SiO_2$, or mixtures thereof. The catalyst system according to the invention may, if desired, comprise internal donors, such as ether or ester compounds or such as, for example, ethyl benzoate, dimethyl phthalate or donors familiar to the person skilled in the art, and, if desired, also external donors from the $RSi(OR)_3$ group, such as $PhSi(OEt)_3$, or external donors familiar to the person skilled in the art.

The present invention relates, in particular, to the use of a catalyst system of this type in heterogeneous propylene polymerisation reactions.

The nitrogen-containing organoaluminium complexes of the general formula (I) according to the invention can be employed in these reactions as cocatalyst and simultaneously also as stereoselectivity promoter. The polymer properties can be controlled through targeted selection of the cocatalyst. Surprisingly, it has been found that the molecular weights of the polypropenes prepared using the cocatalysts according to the invention are much higher than the molecular weights of the polypropenes prepared by means of $AlEt_3$. The nitrogen-containing organoaluminium complexes according to the invention are thus particularly suitable for the preparation of relatively high-molecular-weight polypropene.

The present invention furthermore relates to a process for the preparation of catalyst systems according to the invention for the polymerisation of propene.

Depending on the application, the catalyst systems can be prepared by (a) supporting a titanium halide or vanadium halide on $MgCl_2$ or $SiO_2$ or on a combination of $SiO_2$ and $MgCl_2$, if desired with addition of an internal donor, such as ether or ester compounds, such as ethyl benzoate, dimethyl phthalate, or internal donors familiar to the person skilled in the art, and, if desired, also external donors from the $RSi(OR)_3$ group, such as $PhSi(OEt)_3$, or external donors familiar to the person skilled in the art, and an organoaluminium compound of the general formula (I), or by (b) supporting an organoaluminium compound of the general formula (I) on $MgCl_2$, $SiO_2$ or $SiO_2$ in combination with $MgCl_2$ and addition of a titanium halide or vanadium halide and addition of an internal donor, such as ether or ester compounds, such as ethyl benzoate, dimethyl phthalate, or internal donors familiar to the person skilled in the art, and, if desired, also external donors from the $RSi(OR)_3$ group, such as $PhSi(OEt)_3$, or external donors familiar to the person skilled in the art, or by (c) supporting an active species generated from an organoaluminium compound of the general formula (I) and a titanium halide or vanadium halide on $MgCl_2$ or $SiO_2$ or on a combination of $SiO_2$ and $MgCl_2$ with addition of an internal donor; such as ether or ester compounds, such as ethyl benzoate, dimethyl phthalate, or internal donors familiar to the person skilled in the art, and, if desired, also external donors from the $RSi(OR)_3$ group, such as $PhSi(OEt)_3$, or external donors familiar to the person skilled in the art.

Surprisingly, it has been found that on use of the nitrogen-containing organoaluminium compounds of the general formula (I) in the presence of a titanium halide or vanadium halide compound supported on magnesium dichloride or $SiO_2$ or on a combination of $SiO_2$ and $MgCl_2$, if desired also with use of an internal donor, such as ether or ester compounds, such as ethyl benzoate, dimethyl phthalate, or internal donors familiar to the person skilled in the art, and, if desired, also external donors from the $RSi(OR)_3$ group, such as $PhSi(OEt)_3$, or external donors familiar to the person skilled in the art, a catalyst system is formed which is highly suitable for the polymerisation of propene and at the same time enables yields which are substantially higher than those achieved by the conventional $MgCl_2/TiCl_4/AlEt_3$ comparative system. Various supporting methods have been developed:

(a) supporting a titanium halide or vanadium halide on $MgCl_2$ or $SiO_2$ or on a combination of $SiO_2$ and $MgCl_2$ with addition of an internal donor, such as ether or ester compounds, such as ethyl benzoate, dimethyl phthalate, or internal donors familiar to the person skilled in the art, and, if desired, also external donors from the $RSi(OR)_3$ group, such as $PhSi(OEt)_3$, or external donors familiar to the person skilled in the art, and addition of the nitrogen-containing organoaluminium compound of the general formula (I), (b) supporting the nitrogen-containing organoaluminium compound of the general formula (I) on $MgCl_2$ or $SiO_2$ or on a combination of $SiO_2$ and $MgCl_2$ and addition of a titanium halide or vanadium halide and addition of an internal donor, such as ether or ester compounds, such as ethyl benzoate, dimethyl phthalate, or internal donors familiar to the person skilled in the art, and, if desired, also external donors from the $RSi(OR)_3$ group, such as $PhSi(OEt)_3$, or external donors familiar to the person skilled in the art, and (c) supporting an active species already generated from the two components on $MgCl_2$ or $SiO_2$ or on a combination of $SiO_2$ and $MgCl_2$ with addition of an internal donor, such as ether or ester compounds, such as ethyl benzoate, dimethyl phthalate, or internal donors familiar to the person skilled in the art, and, if desired, also external donors from the $RSi(OR)_3$ group, such as $PhSi(OEt)_3$, or external donors familiar to the person skilled in the art.

The experiments carried out have shown that method (a) gives the highest activities during the polymerisation of propene. Virtually double the activities can be obtained compared with the prior art. In particular, very high activities are obtained at low Al:Ti ratios; for example, the activities at an Al:Ti ratio of 2:1 are a factor of 10-18 higher than the prior art. The experiments have furthermore shown that method (b) gives polypropenes having the highest pentad isotacticities. This shows that the supported nitrogen-containing organoaluminium complexes of the general formula (I) block titanium centres working aspecifically via the nitrogen atom. This positive effect does not occur in the nitrogen-free reference system $AlEt_3$.

It has been found that the properties of the polypropylenes can be controlled through the choice of cocatalyst.

The catalyst systems according to the invention can advantageously be employed under process-simplifying conditions. The latter is, in particular, the case on use of a lower cocatalyst/catalyst ratio than usual hitherto. The polymerisation properties can be controlled in accordance with the invention by, in particular, a change in this ratio.

As a further advantageous property, it has been found that the novel catalyst systems are fairly stable to air, moisture and impurities in the reaction system and thus require technically less complex containers for storage and transport or technically less complex plants for catalyst preparation and for olefin polymerisation. The novel catalyst systems also have high thermal stability and a long service life under reaction conditions.

It has furthermore been found, surprisingly, that the novel catalyst systems consisting of $MgCl_2$ or $SiO_2$ or a combination of $SiO_2$ and $MgCl_2$, a titanium halide or vanadium halide compound, an internal donor and an aluminium compound of the general formula (I) also act stereoselectively during the polymerisation of propene without the addition of external donors.

The organoaluminium compounds of the general formula (I) can thus simultaneously take on a number of functions in the novel catalyst systems:

On the one hand, they act as cocatalysts and on the other hand, they act as stereoselectivity promoters. It is thus possible to reduce the number of requisite catalyst components by one component. The third function consists in control of the molecular structure of the polymers, such as molecular weights, molecular-weight distributions, tacticities and branches, and thus of the polymer properties, such as hardness, rigidity, toughness, weldability, transparency, gas permeability and processability.

Besides the higher thermal stability and lower oxygen and moisture sensitivity found, a reduction in the number of catalyst components additionally contributes to a general process simplification in catalyst preparation and propene polymerisation.

The low oxygen and moisture sensitivity of the aluminium compounds of the general formula (I), which facilitates easier and safer handling, is achieved by the intramolecular-stabilising amino group with coordinative stabilisation of the aluminium centre.

The nitrogen-containing organoaluminium complexes of the general formula (I) according to the invention in which R and R', independently of one another, are $CH_3$, $C_2H_5$ or i-$C_4H_5$, $R^1$ and $R^{1'}$, independently of one another, are $CH_3$ or $C_2H_5$, $R^2$ is an unsubstituted hydrocarbon selected from the group consisting of

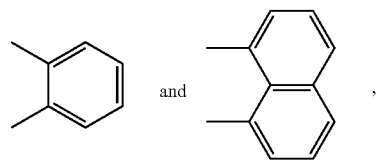

$R^3$ and $R^4$ are $CH_2$, and, independently of one another, m and n=0 or 1 and o=1, can be prepared in a simple manner by reacting a compound of the general formula (II)

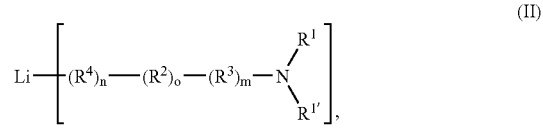

(II)

in which $R^1$, $R^{1'}$, $R^2$, $R^3$ and $R^4$ are as defined above, with a compound of the general formula (III)

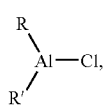
(III)

in which R and R' are as defined above, in an aprotic solvent at a temperature in the range from −50 to +30° C., and separating off the resultant reaction product. The reaction is preferably carried out under a protective-gas atmosphere. Protective gases which can be used here -are nitrogen gas or noble gases, such as helium or argon. The starting materials are preferably employed in the reaction in an equimolar ratio to one another. Depending on the reactivity of the two reactants, however, it may also be appropriate to add a compound of the general formula (III) in excess to the reaction mixture.

The aprotic solvents used for carrying out the reaction can be solvents selected from the group consisting of toluene, xylene, pentane, cyclopentane, hexane, cyclohexane and heptane, or mixtures thereof.

In order to achieve the most complete reaction possible, it is appropriate to stir the reaction mixture for some time without cooling after the two reactants have been mixed at low temperature, during which the reaction mixture may warm to room temperature.

The reaction products formed by the reaction can be separated off and, if necessary, purified by methods known to the person skilled in the art.

The separation is preferably carried out by distillative methods. The products are particularly preferably separated off by fractional distillation. Depending on the boiling point of the reaction product formed, this distillation is carried out under reduced pressure.

As described, the novel catalyst systems consist of support, catalyst, donor and cocatalyst:

The cocatalysts used are the nitrogen-stabilised organoaluminium compounds of the general formula (I), in which, independently of one another, three organyl groups are covalently bonded to the aluminium atom. One of these organyl groups carries at the end an amino function, which is coordinatively bonded to the aluminium atom via the nitrogen atom, forming a cyclic structural unit. Two organyl substituents which are independent of one another are bonded to the amino group. The organyl unit between the aluminium atom and the nitrogen atom can include, for example, a naphthyl, phenyl, benzyl or alkyl group, which is unsubstituted or mono- or polyalkylated or -fluorinated. Preference is given to compounds which have an aromatic group in this organyl unit.

The catalysts used are transition-metal compounds from sub-groups IV to VIII of the Periodic Table of the Elements, in particular transition-metal compounds from sub-groups IV and V of the Periodic Table, in particular titanium halide and vanadium halide compounds. Suitable compounds are, for example, $TiCl_4$ and $VCl_4$.

The catalyst support used can be anhydrous $MgCl_2$ or $SiO_2$ or a combination of $SiO_2$ and $MgCl_2$.

The donors used are internal donors, such as ether or ester compounds, such as ethyl benzoate, dimethyl phthalate, or internal donors familiar to the person skilled in the art, and, if desired, also external donors from the $RSi(OR)_3$ group, such as $PhSi(OEt)_3$, or other external donors familiar to the person skilled in the art.

The supported catalyst systems according to the invention are prepared by a process which is disclosed with reference to examples given in the following text. These examples represent specific embodiments. The expert knowledge of the person skilled in the art enables him to replace the agents given therein by corresponding agents having the same action.

Solvents which can be used for the preparation of the supported catalyst systems are aprotic, nonpolar solvents, such as pentane, hexane, heptane, octane, benzene, toluene or xylene.

It has been found that effective systems are obtained if the cocatalyst/catalyst ratio is between 1:1 and 80:1, preferably between 2:1 and 20:1.

It has been found that the use of the nitrogen-containing organoaluminium compounds of the general formula (I) as cocatalysts in the polymerisation of propene results in an increase in activity to virtually double compared with the conventional catalyst systems on use of conventional Al:Ti ratios. In addition, the cocatalyst/catalyst ratio in the catalyst systems can be reduced to 1:1 or 2:1 without resulting in losses of activity. The activities obtained at these low Al:Ti ratios are a factor of 10 to 18 higher than the activities obtained with $AlEt_3$. In this way, higher yields of polypropylene can be achieved, and the amount of cocatalyst in the catalyst systems can be drastically reduced. The catalyst systems according to the invention can thus be prepared significantly less expensively than corresponding systems known to date. It is possible to reduce the cocatalyst/catalyst ratio to values between 5:1 and 1:1 without significantly influencing the yields and the target quality of the products.

Polypropenes having significantly higher molecular weights of between 200,000 and 800,000 g/mol are obtained.

The catalyst concentration is between $10^{-2}$ and $10^{-6}$ mol/l, preferably between $10^{-3}$ and $10^{-5}$ mol/l.

The catalyst or cocatalyst loading on $MgCl_2$ is between 0.5 and 5 mmol/g, preferably between 1 and 3 mmol/g.

Due to their lower moisture and air sensitivity and due to their lower sensitivity to impurities during use in a polymerisation, the novel catalyst systems enable safer handling and better reproducibility of the results, but also higher long-term stability compared with the systems of the prior art.

For better understanding and in order to illustrate the invention, examples are given below which are within the scope of protection of the present invention. However, owing to the general validity of the inventive principle described, these are not suitable for reducing the scope of protection of the present application merely to these examples. Furthermore, the contents of the cited patent application P 10010796 should be regarded as part of the disclosure of the invention of the present description.

Examples of the Preparation of the Catalyst Systems:

a) Preparation of the Novel Cocatalysts:

[2-(Diethylaminomethyl)phen-1-yl]diethylaluminium

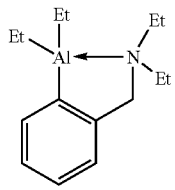

10.1 ml (88.54 mmol) of diethylaluminium chloride were added dropwise to a suspension, cooled to −10° C., of 14.98 g (88.54 mmol) of [2-(diethylaminomethyl)phen-1-yl]lithium in 130 ml of toluene in an inert nitrogen atmosphere (other inert gases, such as, for example, argon, are also suitable as protective gas). After slow warming to room temperature, the mixture was stirred for 16 hours in order to complete the reaction. Filtration through a D4 frit and removal of the solvent by distillation gave 17.64 g of [2-(diethylaminomethyl)phen-1-yl]diethylaluminium (71.3 mmol/81%) as a colourless liquid by slow fractional distillation from the residue.

b.p.: 115° C./4·10$^{-2}$ mbar $^1$H-NMR (C$_6$D$_6$, 200.1 MHz): δ 0.16-0.29 [m, 4H, Al(CHH'CH$_3$)$_2$]; 0.53 [t, $^3$J=7.31 Hz, 6H, Al(CH$_2$CH$_3$)$_2$]; 1.40 [t, $^3$J=8.17 Hz, 6H, N(CH$_2$CH$_3$)$_2$]; 2.18-2.52 [m, 4H, N(CHH'CH$_3$)$_2$]; 3.34 (s, 2H, NCH$_2$); 6.68-6.91 (m, 1H, H$_{ar}$); 7.19-7.24 (m, 2H, H$_{ar}$); 7.88-7.93 (m, 1 H, H$_{ar}$).

$^{13}$C-NMR (C$_6$D$_6$, 50.32 MHz): δ 0.3 [Al(CH$_2$ $_{CH3}$)$_2$]; 8.1, 10.3 [Al(CH$_2$ $_{CH3}$)$_2$, N(CH$_2$CH$_3$)$_2$]; 44.2 [N(CH$_2$ $_{CH3}$)$_2$]; 60.6 (NCH$_2$); 123.7, 126.8, 127.2, 128.3, 137.4, 143.6 (C$_{ar}$).

$^{27}$Al-NMR (C$_6$D$_6$, 104.3 MHz): δ 172.

[2-(Dimethylaminomethyl)phen-1-yl]diisobutylaluminium

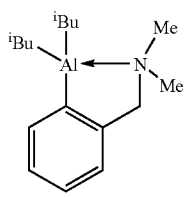

20 ml (102.5 mmol) of diisobutylaluminium chloride were added dropwise to a suspension, cooled to 0° C., of 15.36 g (108.8 mmol) of [2-(dimethylaminomethyl)phen-1-yl]lithium in 400 ml of pentane in an inert nitrogen atmosphere (other inert gases, such as, for example, argon, are also suitable as protective gas). After slow warming to room temperature, the mixture was stirred for 40 hours in order to complete the reaction. Filtration through a D4 frit and removal of the solvent by distillation gave 23.94 g of [2-(dimethylaminomethyl)phen-1-yl]diisobutylaluminium (85%) as a colourless liquid by slow fractional distillation from the residue.

b.p.: 102-107° C./2·10$^{-2}$ mbar $^1$H-NMR (C$_6$D$_6$, 200.1 MHz): δ 0.21 [2×dd, 4H, Al(CHH')$_2$]; 1.21 [2×d, 12H, Al(CH$_2$CHCH$_3$CH$_3$')$_2$]; 1.78 [s, 6H, N(CH$_3$)$_2$]; 2.09 [septet, 2 H, Al(CH$_2$CH)$_2$]; 3.17 (s, 2H, NCH$_2$); 6.85 (dd, 1H, C$_{ar}$H-3); 7.21 (m, 2 H, C$_{ar}$H-4,5); 7.91 (dd, 1H, C$_{ar}$H-6).

$^{13}$C-NMR (C$_6$D$_6$, 50.32 MHz): δ 21.5 [broad, Al(CH$_2$ $_{)2}$]; 27.1 [Al(CH$_2$ $_{CH)2}$; 28.8 (AlCH$_2$CHCH$_3$CH$_3$')$_2$]; 28.9 (AlCH$_2$CHCH$_3$CH$_3$')$_2$]; 45.4 [N(CH$_3$)$_2$]; 67.5 (NCH$_2$); 123.8 (CH$_{ar}$); 127.0 (CH$_{ar}$); 137.5 (CH$_{ar}$); 143.5 (CH$_2$C$_{ar}$); 152.5 (very broad, AlC$_{ar}$).

$^{27}$Al-NMR (C$_6$D$_6$, 104.3 MHz): δ 181.

[2-(Dimethylamino)benzyl]dimethylaluminium

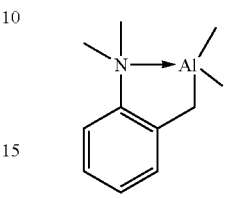

10.0 ml (107.8 mmol) of dimethylaluminium chloride were added dropwise to a suspension, cooled to −30° C., of 15.21 g (107.8 mmol) of [2-(dimethylamino)benzyl]lithium in 250 ml of hexane in an inert nitrogen atmosphere. After slow warming to room temperature, the mixture was stirred for 14 hours in order to complete the reaction. Filtration through a D4 frit and removal of the solvent by distillation gave 11.95 g of [2-(dimethyl-amino)benzyl]dimethylaluminium (62.5 mmol/58%) as a colourless liquid by slow fractional distillation from the residue.

b.p.: 58° C./2·10$^{-2}$ mbar $^1$H-NMR (C$_6$D$_6$, 200.1 MHz): δ 0.55 [s, 6H, Al(CH$_3$)$_2$]; 1.47 (s, 2H, AlCH$_2$); 2.09 [s, 6H, N(CH$_3$)$_2$]; 6.58-6.63 (m, 1H, H$_{ar}$); 6.83-7.01 (m, 2H, H$_{ar}$); 7.26-7.30 (m, 1H, H$_{ar}$).

$^{13}$C-NMR (C$_6$D$_6$, 50.32 MHz): δ 10.7 [Al(CH$_3$)$_2$]; 13.8 (AlCH$_2$); 46.3 [N(CH$_3$)$_2$]; 118.0, 124.8, 127.4, 132.9, 143.0, 149.0 (C$_{ar}$).

$^{27}$Al-NMR (C$_6$D$_6$, 104.3 MHz): δ 189.

[2-(Dimethylamino)benzyl]diethylaluminium

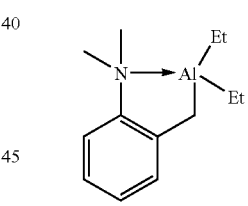

7.17 g (7.5 ml; 59.5 mmol) of diethylaluminium chloride were added dropwise to a suspension, cooled to −30° C., of 8.40 g (59.5 mmol) of 2-dimethylaminobenzyllithium in 150 ml of toluene in an inert nitrogen atmosphere. After slow warming to room temperature, the mixture was stirred for 15 hours in order to complete the reaction. Filtration through a D4 frit and removal of the solvent by distillation gave 8:05 g of [2-(dimethylamino)benzyl]-diethylaluminium (36.7 mmol/62%) as a colourless liquid by slow fractional distillation from the residue.

b.p.: 92° C./2·10$^{-2}$ mbar $^1$H-NMR (C$_6$D$_6$; 200.1 MHz): δ-0.06-0.23 [m, 4H, Al(CHH'CH$_3$)$_2$]; 1.22 [t, $^3$J=8.2 Hz, 6H, Al(CH$_2$CH$_3$)$_2$]; 1.45 (s, 2H, AlCH$_2$N); 2.14 [s, 6H, N(CH$_3$)$_2$]; 6.59-6.63 (m, 1H, H$_{ar}$); 6.82-7.00 (m, 2H, H$_{ar}$); 7.25-7.29 (m, 1H, H$_{ar}$).

$^{13}$C-NMR (C$_6$D$_6$; 50.32 MHz): 6-0.8 [Al(CH$_2$ $_{CH3}$)$_2$]; 9.9 [AlCH$_2$N]; 11.4 [Al(CH$_2$ $_{CH3}$)$_2$]; 46.3 [N(CH$_3$)$_2$]; 117.6; 124.7; 127.5; 132.9; 143.2; 149.1 (C$_{ar}$). $^{27}$Al-NMR (C$_6$D$_6$; 104.3 MHz): δ 185.

[8-(Dimethylamino)naphth-1-yl]diisobutylaluminium

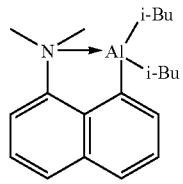

9.5 g (0.048 mmol) of diisobutylaluminium chloride were added dropwise to a suspension, cooled to −40° C., of 12.1 g (0.048 mmol) of [8-(dimethylamino)naphth-1-yl]lithium etherate and 100 ml of diethyl ether in an inert nitrogen atmosphere. After slow warming to room temperature, the mixture was stirred for a further 24 hours in order to complete the reaction. Filtration through a D4 frit and removal of the solvent by distillation gave 10.6 g of [8-(dimethylamino)naphth-1-yl]diisobutylaluminium (71%) as a colourless, oily liquid by fractional distillation from the residue.

b.p.: 147° C./$10^{-2}$ mbar $^1$H-NMR (200.1 MHz, $C_6D_6$): δ 0.20 [ABX, 2H, $^3$J 6.9 Hz, $^2$J 14.0 Hz (($CH_3$)$_2$—CH—CHH')$_2$Al]; d 0.36 [ABX, 2H, $^3$J 6.9 Hz, $^2$J 14.0 Hz (($CH_3$)$_2$—CH—CHH')$_2$Al]; 1.18 [d, 12H, $^3$J 6.7 Hz, (($CH_3$)$_2$—CH—CHH')$_2$ Al]; 2.06 [m, ABX, 2H, $^3$J 6.7 Hz, $^3$J 6.9 Hz, (($CH_3$)$_2$—CH—CHH')$_2$Al]; 2.28 [s, 6H, —N($CH_3$)$_2$]; 6.74 (dd, $^3$J 7.5 Hz, $^4$J 1 Hz, 1H, H—$C_7$); 7.13 (dd, $^3$J 8.2 Hz, $^3$J 7.5 Hz, 1H, H—$C_6$);); 7.47 (dd, $^3$J 8.2 Hz, $^3$J 6.2 Hz, 1H, H—$C_3$); 7.55 (dd, $^3$J 8.2 Hz, $^4$J 1 Hz, 1H, H—$C_5$); 7.60 (dd, $^3$J 8.2 Hz, $^4$J 1.3 Hz, 1H, H—$C_4$); 8.08 (dd, $^3$J 6.2 Hz, $^4$J 1.3 Hz, 1H, H—$C_2$).

$^{13}$C-NMR (100.6 MHz, $C_6D_6$): δ 22.66 [broad, (($CH_3$)$_2$—CH—$CH_2$)$_2$Al]; 27.12 [($CH_3$)$_2$—CH—$CH_2$)$_2$Al]; 28.85 [($CH_3$)$_2$—CH—$CH_2$)$_2$Al]; 49.00 [—N($CH_3$)$_2$]; 114.27 ($C_7$); 124.73 ($C_6$); 125.92 ($C_4$); 127.81 ($C_5$); 127.86 ($C_3$); 133.61 ($C_{10}$); 135.17 ($C_2$); 137.31 ($C_9$); 149.8 (very broad, $C_1$); 151.25 ($C_8$).

$^{27}$Al-NMR (104.3 MHz, $C_6D_6$): δ 195 ($W_{1/2}$=13.000 Hz).

b) Supporting of the Organoaluminium Complexes of the General Formula (I) on $MgCl_2$ Organoaluminium compound: $n_{Al\ cocat}$[mol]=$m_{Al\ cocat}$/$M_{Al\ coat}$ $MgCl_2$: $m_{MgCl2}$=$n_{Al\ cocat}$/theor. loading [mol(Al)/g]−$m_{Al\ cocat}$ Hydrocarbon: for 3-8 g total amount ($m_{MgCl2}$+$m_{Al\ cocat}$)50 ml All work is carried out under a protective gas. The hydrocarbon used is dried and distilled before the reaction. The organoaluminium compound and the magnesium chloride are introduced into a heat-dried flask with Schlenk attachment. The corresponding amounts are calculated from the desired theoretical loading, which should be in the range 1-2*$10^{-3}$ mol (Al)/g. Depending on the solubility of the organoaluminium compound, pentane, hexane, heptane, octane, benzene or toluene is added. The reaction mixture is then stirred at room temperature for 12 hours. The solvent is subsequently removed under reduced pressure at 60-120 mbar.

The theoretical loading is calculated in accordance with the following equation:

$(m_{Al\ cocat}/M_{Al\ cocat})/(m_{Al\ cocat}+m_{MgCl2})$=theor. loading [mol(Al)/g]

| Supported component | Loading [mmol/g] | Supported component | Loading [mmol/g] |
|---|---|---|---|
| | 1.5 | | 1.0 |

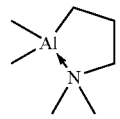

Supporting of (3-dimethylaminopropyl)dimethylaluminium on $MgCl_2$

Al cocat: 1.77 g (1.2*$10^{-2}$ mol) $M_{Al\ cocat}$=143.21 g/mol $MgCl_2$: 6.50 g (6.8*$10^{-2}$ mol) $M_{MgCl2}$=95.21 g/mol Pentane: 50 ml All work was carried out under a protective gas. Pentane was dried and distilled before the reaction. The organoaluminium compound and the magnesium chloride were introduced into a heat-dried 100 ml flask with Schlenk attachment. After addition of 50 ml of pentane, the reaction mixture was stirred at room temperature for 0.12 hours. The solvent was subsequently removed for 2 hours under reduced pressure at 100-120 mbar, giving a pale-grey powder.

The theoretical loading was calculated in accordance with the following equation:

$(m_{Al\ cocat}/M_{Al\ cocat})/(m_{Al\ cocat}+m_{MgCl2})$=1.5*$10^{-3}$ mol/g c) Supporting of $TiCl_4$ on $MgCl_2$ Suspend $MgCl_2$ in 50 ml of pentane, add $TiCl_4$, stir for 12 hours at 25° C. under an inert-gas atmosphere, remove pentane at 80 mbar. Loading: 1.4 mmol/g.

Examples of the Use of the Novel Catalyst Systems in the Polymerisation of Propene:

The polymerisation of propene is carried out continuously or discontinuously in a known manner by solution, suspension or gas-phase polymerisation at a temperature of from 0° C. to +200° C., preferably between +20 and +140° C., and a pressure of from 1 to 20 bar, preferably from 2 to 10 bar. The solvent used is hexane, heptane, octane, propene or toluene.

The novel catalyst systems enable the preparation of homopolymers, copolymers and block polymers, preferably homopolymers, of polypropylene.

The activities of the catalyst systems in the polymerisation of propylene are higher than with the conventional catalyst system comprising $MgCl_2$, $TiCl_4$ and $AlEt_3$, even using a lower cocatalyst/catalyst ratio.

With all novel catalyst systems, finely particulate polymers were obtained. The melting points and molecular weights of the polypropenes are in interesting ranges with respect to their industrial processing.

The polypropenes prepared using the nitrogen-stabilised organoaluminium compounds supported on $MgCl_2$ have higher pentad isotacticities than when they are used in dissolved form with $MgCl_2/TiCl_4$. In some cases, higher stereoselectivities are achieved than with $AlEt_3$ as cocatalyst. This result may be caused by the effective blocking of aspecifically working Ti centres on the surface of $MgCl_2$ by means of the nitrogen-stabilised organoaluminium compounds.

Although higher stereoselectivities can be achieved with supported nitrogen-stabilised organoaluminium compounds, the polymerisation with $MgCl_2/TiCl_4$ and dissolved nitrogen-stabilised organoaluminium compounds should be given priority since it generally results in greater activities.

The catalyst systems have a stereoselective action in the polymerisation of propylene without addition of donors. $^{13}$C-NMR analyses of the polypropylene samples show linear structures with isotactic sequence lengths with a significantly higher frequently of the mmmm pentads compared with $AlEt_3$. A further improvement in the stereoselectivities can be achieved through the use of donors.

Performance of the Polymerisation of Propylene

All polymerisations were carried out under an argon inert-gas atmosphere using Schlenk techniques. The polymerisations were carried out in a 1 l Büchi glass autoclave. The reactor was evacuated for one hour in an oil-pump vacuum at 95° C. before each experiment and flushed a number of times with argon in the interim. The autoclave was filled successively with solvent and the supported cocatalyst suspended in solvent. The monomer was then injected at the desired pressure. After saturation of the suspension located in the reactor with the monomer, the polymerisation was initiated by injection of a solution of $TiCl_4$. In the experiments with dissolved alkylaluminium compounds and supported $TiCl_4$, the addition of the catalyst suspension was carried out first. The polymerisations were then initiated by injection of a solution of the cocatalyst. Performance of the reaction at constant pressure was ensured by the monomer supply to the reactor consisting of a pressure regulator and a Brooks Instruments mass-flow regulator.

The polymerisations were terminated by injection of 5 ml of ethanol. Dilute hydrochloric acid was added to the polymerisation suspension, which was stirred overnight. The organic phase was neutralised using saturated sodium hydrogencarbonate solution and washed with water. The solvent was removed in an oil-pump vacuum to constant weight of the polymer.

Polymer Analysis

The thermograms were recorded using a Meftler-Toledo 821e differential calorimeter at a heating rate of 20° C./min. The values obtained in the 2nd heating phase were quoted as melting points.

The viscosity average molecular weights $M_\eta$ were determined with the aid of an Ubbelohde viscometer. The samples were prepared by dissolving about 50 mg of the polymer in 50 ml of decahydronaphthalene. The flow times were measured by means of a LAUDA Viskoboy. The Mark-Houwink constants were taken from T. G. Scholte, N. L. J. Meijerink, H. M. Schoeffeleers, A. M. G. Brands, *J. Appl. Polym. Sci.* 29 (1984) 3763.

The $^{13}$C-NMR spectra were recorded using a BRUKER MSL 300 instrument. During the measurement, 1000 scans at a measurement frequency of 75.47 MHz and a temperature of 100° C. were usually recorded. The pulse angle was 60° and the relaxation delay was 6 seconds. The NMR samples were prepared by making up a solution of 10 percent by weight of polymer in a mixture of perchlorobutadiene and 1,1,2,2-tetrachlorodideuteroethane.

TABLE 1

Polymerisation of propylene using $MgCl_2$-supported organoaluminium compounds and $TiCl_4$ at 30° C.

| Cocatalyst | Activity [$kg_{PP}/(mol_{Ti}$ $c_{propene}$ h)] | $T_m$ [° C.] | Crystallinity [%] | $\eta$ [ml/g] | $M_\mu$ [g/mol] |
|---|---|---|---|---|---|
|  | 8 | 153 | 24 | 333 | 704,000 |
| Comparison $AlEt_3$ | 62 | 152 | 12 | 217 | 388,000 |

Polymerisation conditions: $T_p$ = 30° C., $P_{monomer}$ = 2 bar, $c_{Ti}$ = $10^{-5}$ mol/l, Al/Ti = 5, $t_p$ = 60 min.

TABLE 2

Microstructure of the polypropenes obtained using $MgCl_2$/organoaluminium compounds and $TiCl_4$:

| | $n_{iso}$ | Rel. int. [%] | Pentads |||||||||
|---|---|---|---|---|---|---|---|---|---|---|---|
| | | | mmmm | mmmr | rmmr | mmrr | rmrr + mrmm | mmrr | mrmr | rrrr | rrrm | mrrm |
| 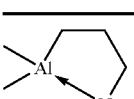 | 10 | Rel. int. [%] | 57.9 | 9.1 | 1.4 | 0.0 | 9.7 | | 6.0 | 2.7 | 8.0 | 5.3 |
| Comp. $AlEt_3$ | 7 | Rel. int. [%] | 46.5 | 10.9 | 2.9 | 0.0 | 12.8 | | 8.7 | 2.9 | 8.7 | 6.5 |

TABLE 3

Polymerisation of propylene using $MgCl_2/TiCl_4$ and organoaluminium compounds at 30° C.

| Cocatalyst | Activity [$kg_{PP}/(mol_{Ti}\, c_{propene}\, h)$] | $T_m$ [° C.] | Crystallinity [%] | $M_\eta$ [g/mol] | $M_w/M_n$ |
|---|---|---|---|---|---|
|  | 145 | 154 | 8 | 634,000 | 13.4 |
|  | 150 | 152 | 8 | 472,000 | 11.5 |
| Comp. $AlEt_3$ | 155 | 151 | 10 | 312,000 | 28.4 |

Polymerisation conditions: $T_p$ = 30° C. in toluene, $P_{monomer}$ = 2 bar, $c_{Ti}$ = $10^{-5}$ mol/l, Al/Ti = 5

TABLE 4

The microstructure of the polypropenes obtained using $MgCl_2/TiCl_4$ and organoaluminium compounds:

| Cocatalyst | $n_{iso}$ | Rel. int. [%] | mmmm | mmmr | rmmr | mmrr | rmrr + mrmm | mrmr | rrrr | rrrm | mrrm |
|---|---|---|---|---|---|---|---|---|---|---|---|
|  | 8 | Rel. int. [%] | 54.3 | 11.7 | 4.7 | 11.3 | 6.4 | 2.9 | 2.5 | 3.8 | 2.4 |
| 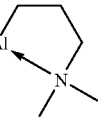 | 6 | Rel. int. [%] | 45.4 | 9.1 | 2.4 | 11.3 | 7.2 | 2.2 | 11.2 | 2.0 | 9.3 |
| Comp. $AlEt_3$ | 7 | Rel. int. [%] | 51.0 | 8.1 | 2.0 | 10.3 | 6.9 | 1.7 | 11.5 | 5.0 | 3.4 |

FIG. 1 shows polymerisation results with the following variation of the polymerisation temperature during the polymerisation of propylene using $MgCl_2/TiCl_4$ and organoaluminium compounds at 2 bar.

Polymerisation conditions: Al/Ti=5, $p_{propene}$=2 bar, $c^{Ti}$=2.5·10$^{-4}$ mol/l in n-hexane, $t_P$=60 min.

Figure 2:
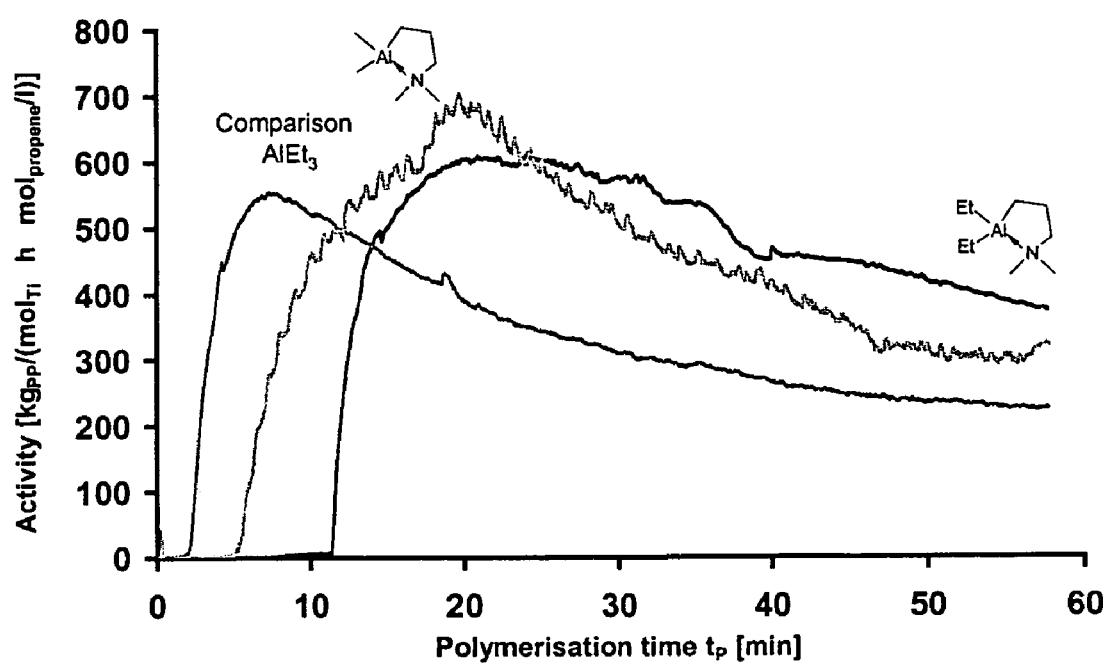

FIG. 2 shows activity curves for the polymerisation of propene at 45° C.

TABLE 5

Properties of the polypropenes obtained

| Cocatalyst | $T_P$ [° C.] | $T_M$ [° C.] | Crystallinity [%] | mmmm [%] | $N_{iso}$ | $M_\eta$ [g/mol] |
|---|---|---|---|---|---|---|
| 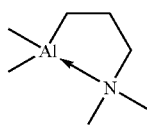 | 30 | 155 | 10 | 34.9 | 4 | 438000 |
| | 45 | 156 | 11 | 37.9 | 5 | 475000 |
| | 60 | 156 | 9 | 40.8 | 5 | 406000 |
| 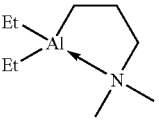 | 30 | 156 | 11 | 47.7 | 7 | 438000 |
| | 45 | 154 | 11 | 45.5 | 7 | 521000 |
| | 60 | 155 | 18 | 43.5 | 8 | 634000 |

TABLE 5-continued

Properties of the polypropenes obtained

| Cocatalyst | $T_P$ [° C.] | $T_M$ [° C.] | Crystallinity [%] | mmmm [%] | $N_{iso}$ | $M_\eta$ [g/mol] |
|---|---|---|---|---|---|---|
| 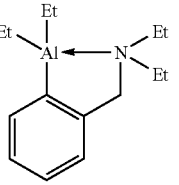 | 60 | 157 | 27 | 40.0 | 5 | 360000 |
| Comp. AlEt$_3$ | 30 | 153 | 12 | 37.6 | 5 | 247000 |
| | 45 | 154 | 16 | 44.0 | 6 | 215000 |
| | 60 | 156 | 26 | 42.3 | 6 | 200000 |

TABLE 6

Variation of the Al/Ti ratio in the polymerisation of propylene using $MgCl_2/TiCl_4$ and organoaluminium compounds at 60° C. and 2 bar.

| Cocatalyst | Al:Ti | Activity [kg$_{PP}$/mol$_{Ti}$·h·mol/l$_{propene}$] | mmmm [%] | $T_m$ [°] | Crystallinity [%] | $M_\eta$ [g/mol] |
|---|---|---|---|---|---|---|
| 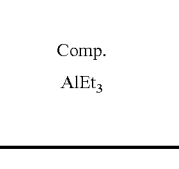 | 1.5 | 223 | — | — | — | — |
| | 2 | 348 | 31 | 154 | 7 | — |
| | 3 | 319 | 39 | 156 | 15 | 477000 |
| | 5 | 279 | 45 | 156 | 16 | 528000 |
| | 10 | 203 | 50 | 156 | 17 | 465000 |
| | 20 | 113 | 55 | 157 | 19 | 710000 |
| 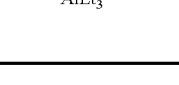 | 2 | 161 | 29 | 154 | 4 | — |
| | 3 | 297 | 37 | 154 | 8 | 340000 |
| | 5 | 405 | 41 | 155 | 12 | 414000 |
| | 10 | 339 | 45 | 156 | 14 | 428000 |
| 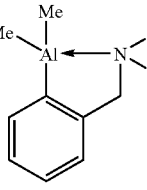 | 5 | 0 | — | — | — | — |
| | 10 | 5 | 30 | 152 | 5 | 264000 |
| | 20 | 55 | 26 | 152 | 2 | 287000 |

TABLE 6-continued

Variation of the Al/Ti ratio in the polymerisation of propylene using MgCl$_2$/TiCl$_4$ and organoaluminium compounds at 60° C. and 2 bar.

| Cocatalyst | Al:Ti | Activity [kg$_{PP}$/mol$_{Ti}$·h·mol/l$_{propene}$] | mmmm [%] | T$_m$ [°] | Crystallinity [%] | M$_\eta$ [g/mol] |
|---|---|---|---|---|---|---|
| 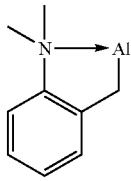 | 2 | 218 | 32 | 152 | 3 | — |
|  | 3 | 275 | 40 | 153 | 7 | 336000 |
|  | 5 | 320 | 45 | 154 | 12 | 419000 |
|  | 10 | 311 | 48 | 154 | 17 | 385000 |
|  | 20 | 295 | 53 | 154 | 15 | 432000 |
| 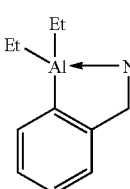 | 2 | 295 | 34 | 152 | 6 | — |
|  | 3 | 347 | 45 | 153 | 6 | 306000 |
|  | 5 | 312 | 47 | 155 | 10 | 523000 |
|  | 10 | 234 | 50 | 156 | 12 | 389000 |
|  | 20 | 120 | 54 | 157 | 16 | 559000 |
| 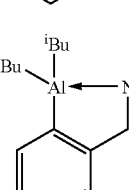 | 3 | 0 | — | — | — | — |
|  | 5 | 63 | 23 | 151 | 1 | 233000 |
|  | 10 | 71 | 21 | 151 | 1 | 249000 |
|  | 20 | 75 | 22 | 152 | 3 | — |
|  | 50 | 83 | 26 | 152 | 6 | 326000 |
| AlEt$_3$ | 2 | 20 | — | — | — | — |
|  | 3 | 269 | 28 | 152 | 2 | 243000 |
|  | 5 | 380 | 40 | 153 | 8 | 191000 |
|  | 10 | 440 | 47 | 153 | 10 | 165000 |
|  | 20 | 456 | 54 | 155 | 18 | 218000 |
|  | 30 | 459 | — | — | — | — |
|  | 50 | 343 | 62 | 157 | 21 | 214000 |

Polymerisation conditions: T$_p$ = 60° C. in n-hexane, p$_{propene}$ = 2 bar, c$_{Ti}$ = 2.5·10$^{-4}$ mol/l, t$_p$ = 60 min.

Figure 3:
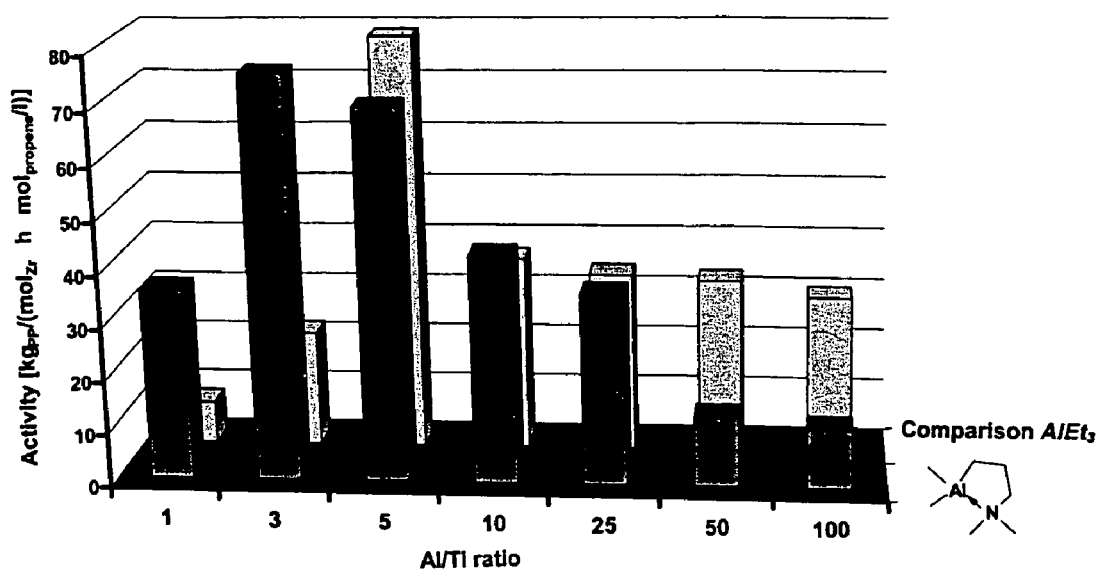

FIG. 3 shows the variation of the Al/Ti ratio in the polymerisation of propylene using MgCl$_2$/TiCl$_4$ and organoaluminium compounds at 60° C. and 6 bar.

Polymerisation conditions: T$_p$=60° C. in n-hexane, P$_{propene}$=6 bar, x$_{Ti}$=5·10$^{-4}$ mol/l, t$_P$=60 min.

TABLE 7

Melting points and crystallinities of the polypropenes obtained

| Al/Ti ratio |  T$_m$ [° C.] | T$_m$ [° C.] AlEt$_3$ | 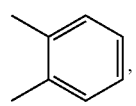 Crystallinity [%] | Crystallinity [%] AlEt$_3$ |
|---|---|---|---|---|
| 1 | 153 | — | 10 | — |
| 3 | 154 | 147 | 14 | 7 |
| 5 | 156 | 153 | 25 | 18 |
| 10 | 156 | 153 | 22 | 20 |
| 25 | 156 | 151 | 17 | 6 |
| 50 | 157 | 153 | 30 | 21 |
| 100 | 156 | — | 38 | — |

The invention claimed is:

1. A nitrogen-containing organoaluminium complex of formula (I)

$$R'\!-\!\underset{R^{1}\ R^{1'}}{\underset{|}{\underset{N}{Al}}}\!-\!(R^{4})_n\!-\!(R^2)_o$$
$$\phantom{xxxxxxxxxxx}|$$
$$\phantom{xxxxxxxxxxxx}(R^3)_m$$

(I)

in which (1) R$^1$ and R$^{1'}$ are CH$_3$,

R and R', independently of one another, are branched or unbranched C$_{3-7}$-alkyl, R$^2$ is

,

R$^3$ CH$_2$, m and o are 1, and n=0;

(2) R$^1$ and R$^{1'}$ are C$_2$H$_5$,

R and R', independently of one another, are branched or unbranched $C_1$-$C_7$-alkyl,
$R^2$ is

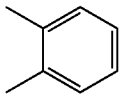

$CH_2$,
m and o =1, and n =o;
(3) R, R', $R^1$ and $R^{1'}$, independently of one another, are branched or unbranched $C_1$-$C_7$-alkyl,
$R^2$ is

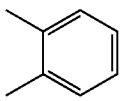

$R^4$ is $CH_2$,
n and o are 1, and
m is 0; or
(4) $R^1$ and $R^{1'}$ are $CH_3$,
R and R', independently of one another, are branched or unbranched $C_3$-$C_7$-alkyl,
or
$R^1$ and $R^{1'}$ are $C_2H_5$
and
R and R', independently of one another, are branched or unbranched $C_1$-$C_7$-alkyl,
$R^2$ is

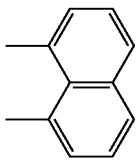

o is 1, and
m and n are 0.

2. A nitrogen-containing organoaluminium complex according to claim 1 of formula (I) (1)
in which
$R^1$ and $R^{1'}$ are $CH_3$ and
R and R', independently of one another, are i-$C_3H_7$, i-$C_4H_9$ or a branched or unbranched alkyl from the group consisting of $C_5H_{11}$, $C_6H_{13}$ and $C_7H_{15}$.

3. A nitrogen-containing organoaluminium complex according to claim 1 of formula (I) (2)
in which
$R^1$ $R^{1'}$ are $C_2H_5$ and
R and R', independently of one another, are $CH_3$, $C_2H_5$ or i-$C_4H_9$.

4. A coordination catalyst system comprising a nitrogen-containing organoaluminium complex of formula (I) according to claim 1 in combination with a transition-metal compound from sub-groups 4 to 10 of the Periodic Table of the Elements.

5. A coordination catalyst system according to claim 4 comprising halides of titanium or vanadium.

6. A coordination catalyst system according to claim 4 bonded to an inorganic support comprising $MgCl_2$, $SiO_2$, or mixtures thereof.

7. A coordination catalyst system according to claim 4, further comprising internal electron donors which are ethers or esters, and, optionally an, external electron donor $RSi(OR)_3$ which is $PhSi(OEt)_3$.

8. A process for the preparation of polypropylene, comprising polymerizing propene under polymerization conditions in the presence of a nitrogen-containing organoaluminium complex of formula (I) according to claim 1.

9. A process for the preparation of nitrogen-containing organoaluminium complexes of formula (I) according to claim 1 comprising reacting a compound of formula (II)

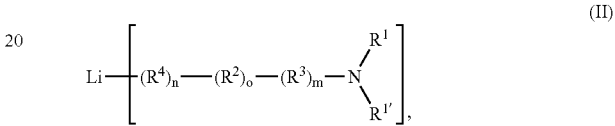

with a compound of formula (III)

in an aprotic solvent at a temperature in the range from −50 to +30° C., and optionally separating the resultant reaction product.

10. A process according to claim 9, wherein the aprotic solvent is toluene, xylene, pentane, cyclopentane, hexane, cyclohexane, heptane, or mixtures thereof.

11. A process according to claim 9, wherein the reaction product formed is separated off by distillation.

12. A process for the preparation of polypropylene, comprising polymerizing propene under polymerization conditions in the presence of a coordination catalyst system according to claim 4.

13. A process for the preparation of a catalyst system for the polymerisation of propene, comprising (a) supporting a titanium halide or vanadium halide on $MgCl_2$ or $SiO_2$ or on a combination of $SiO_2$ and $MgCl_2$, optionally with addition of an internal donor, and an organoaluminium compound of formula (I) according to claim 1 or (b) supporting an organoaluminium compound of formula (I) on $MgCl_2$, $SiO_2$ or $SiO_2$ in combination with $MgCl_2$, and adding a titanium halide or vanadium halide, and adding an internal donor and/or external donor, or (c) generating an active species from an organoaluminium compound of formula (I) and a titanium halide or vanadium halide, and this species on $MgCl_2$ or $SiO_2$ or on a combination of $SiO_2$ and $MgCl_2$ with addition of one or more internal electron donors and, optionally, one or more external electron donors.

14. A process according to claim 13, wherein the supporting is carried out in aprotic, nonpolar solvents.

15. A process according to claim 14, wherein the aprotic, nonpolar solvents are pentane, hexane, heptane, octane, benzene or toluene.

16. A process according to claim 13, wherein the internal electron donors are ethyl benzoate, or dimethyl phthalate, and the external electron donor is $PhSi(OEt)_3$.

* * * * *

UNITED STATES PATENT AND TRADEMARK OFFICE
CERTIFICATE OF CORRECTION

PATENT NO.        : 7,351,678 B2                              Page 1 of 1
APPLICATION NO. : 10/491917
DATED             : April 1, 2008
INVENTOR(S)       : Köhler et al.

It is certified that error appears in the above-identified patent and that said Letters Patent is hereby corrected as shown below:

Title Page Item (75) The first inventor's name reads "Kartin Köhler", should read -- Katrin Köhler --.

Signed and Sealed this

Thirty-first Day of March, 2009

JOHN DOLL
*Acting Director of the United States Patent and Trademark Office*